United States Patent [19]

Pelrine et al.

[11] Patent Number: 4,996,384
[45] Date of Patent: * Feb. 26, 1991

[54] REGENERATION OF REDUCED METAL OXIDE OLIGOMERIZATION CATALYST

[75] Inventors: Bruce P. Pelrine, Trenton; Margaret M. Wu, Belle Mead, both of N.J.

[73] Assignee: Mobil Oil Corporation, Fairfax, Va.

[*] Notice: The portion of the term of this patent subsequent to May 15, 2007 has been disclaimed.

[21] Appl. No.: 481,279

[22] Filed: Feb. 20, 1990

Related U.S. Application Data

[63] Continuation-in-part of Ser. No. 282,362, Dec. 9, 1988, Pat. No. 4,926,004.

[51] Int. Cl.$^5$ ............................................. C07C 2/10
[52] U.S. Cl. ..................................... 585/530; 585/10
[58] Field of Search ................................. 585/10, 530

[56] References Cited

U.S. PATENT DOCUMENTS 4,827,064  5/1989  Wu ........................................ 585/10
4,827,073  5/1989  Wu ........................................ 585/530

*Primary Examiner*—Curtis R. Davis
*Attorney, Agent, or Firm*—Alexander J. McKillop; Charles J. Speciale; Malcolm D. Keen

[57] ABSTRACT

A process for producing oligomers from alpha-olefins, such as 1-decene, in which the olefins are oligomerized over a supported, reduced metal oxide catalyst from Group VIB of the Periodic Table to give oligomers with a branch ratio of less than 0.19. The catalyst, preferably a chromium/silica catalyst the catalyst can be regenerated to allow repeated recycling of the catalyst without a loss in yield of the oligomer product. The regeneration process comprises: (i) purging or stripping the deactivated catalyst with inert gas at elevated temperature to strip unreacted olefin and oligomer product from the catalyst; (ii) contacting the deactivated and purged catalyst with a stream of oxidizing gas while heating to elevated temperature to oxidize the metal component of the catalyst and remove carbonaceous deposits from the catalyst; (iii) cooling the oxidized catalyst and contacting it with a stream of reducing gas to reduce the metal component of the oxidized catalyst to a lower valence state. The oligomerization may be carried out at relatively high temperatures of about 90° to 250° C. to produce liquid lubricant products of high viscosity index, typically above 130, or at lower temperatures from about −20° to about +90° C. to product products of higher molecular weight which may be used as lubricant additives, e.g. VI improvers. The high molecular weight products are generally characterized by a branch ratio less than 0.19, a weight average molecular weight from about 15,000 to 200,000, a number average molecular weight from about 5,000 to about 50,000 and a molecular weight distribution from about 1 to about 5. They are also shear stable under high temperature, high shear rate conditions of 150° C. and a shear rate of $10^6$ second$^{-1}$.

15 Claims, 1 Drawing Sheet

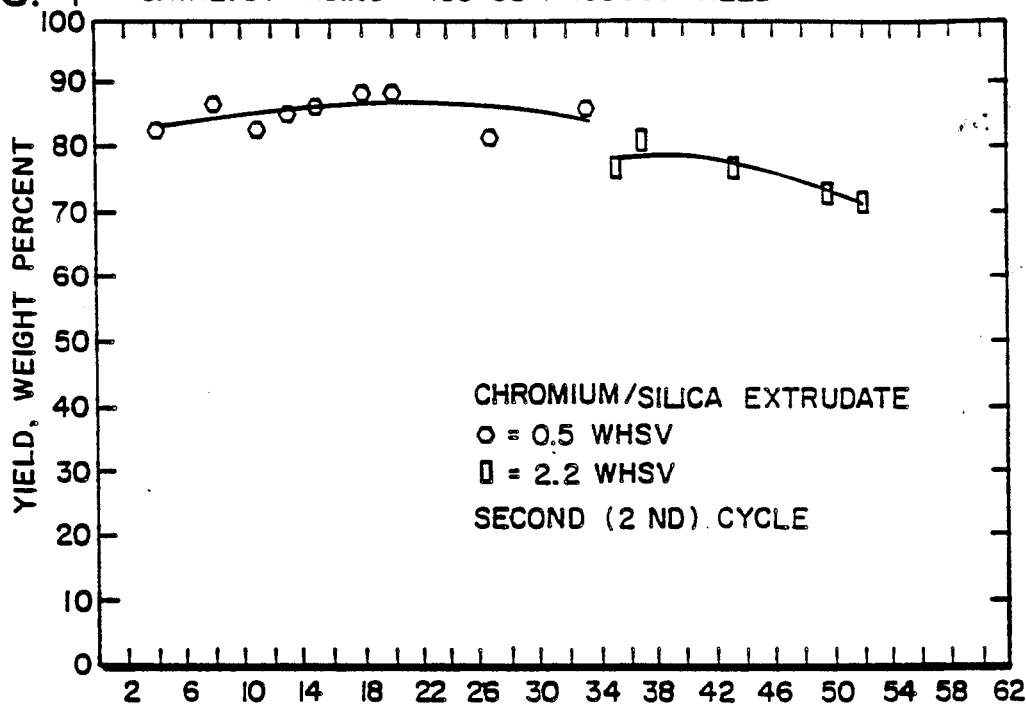
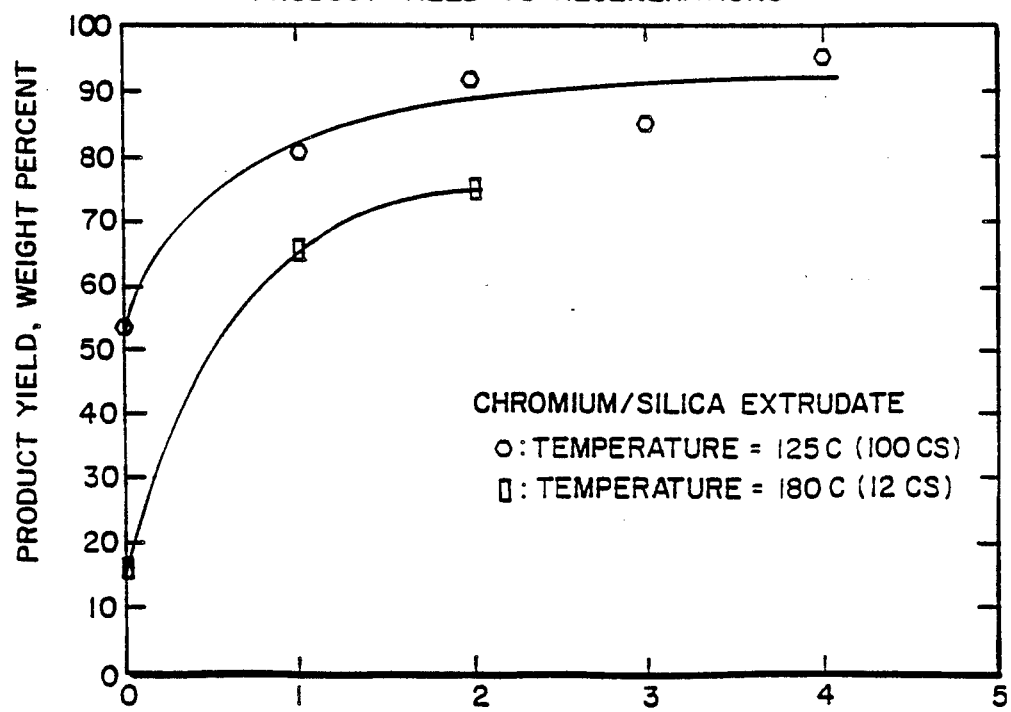

REGENERATION OF REDUCED METAL OXIDE OLIGOMERIZATION CATALYST

CROSS-REFERENCE TO RELATED APPLICATIONS

This application is a continuation-in-part of our prior application Ser. No. 07/282,362, filed December 9, 1988, now U.S. Pat. No. 4,926,004 entitled Regeneration of Reduced Supported Chromium Oxide Catalyst for Alpha-Olefin Oligomerization.

FIELD OF THE INVENTION

This invention relates to novel processes for the production of olfin oligomers which are useful as lubricants and lubricant additives. It relates more particularly to the regeneration of reduced chromium oxide oligomerization catalysts used in the preparation of the olefin oligomers.

BACKGROUND OF THE INVENTION

The catalytic oligomerization of olefins is a known technique for manufacturing hydrocarbon basestocks useful as lubricants. Efforts to improve upon the performance of natural mineral oil based lubricants by the synthesis of oligomeric hydrocarbon fluids have been the subject of important research and development in the petroleum industry for many years and have led to the relatively recent market introduction of a number of superior polyalpha-olefin (PAO) synthetic lubricants, primarily based on the oligomerization of alpha-olefins or 1-alkenes. In terms of lubricant property improvement, the thrust of the industrial research effort on synthetic lubricants has been toward fluids exhibiting useful viscosities over a wide range of temperature, i.e., improved viscosity index (VI), while also showing lubricity, thermal and oxidative stability and pour point equal to or better than mineral oil. These new synthetic lubricants lower friction and hence increase mechanical efficiency across the full spectrum of mechanical loads from worm gears to traction drives and do so over a wider range of operating conditions than mineral oil lubricants.

The chemical focus of the research effort in synthetic lubricants has been on the polymerization of 1-alkenes. Well known structure/property relationships for high polymers as contained in the various disciplines of polymer chemistry have pointed the way to 1-alkenes as a fruitful field of investigation for the synthesis of oligomers with the structure thought to be needed to confer improved lubricant properties on them. Due largely to studies on the polymerization of propene and vinyl monomers, the mechanism of the polymerization of 1-alkene and the effect of that mechanism on polymer structure is reasonably well understood, providing a strong resource for targeting on potentially useful oligomerization methods and oligomer structures. Building on that resource, in the prior art oligomers of 1-alkenes from $C_6$ to $C_{20}$ have been prepared with commercially useful synthetic lubricants from 1-decene oligomerization yielding a distinctly superior lubricant product via either cationic or Ziegler catalyzed polymerization.

One characteristic of the molecular structure of 1-alkene oligomers that has been found to correlate well with improved lubricant properties in commercial synthetic lubricants is the ratio of methyl to methylene groups in the oligomer. The ratio is called the branch ratio and is calculated from infra-red spectral data as discussed in "Standard Hydrocarbons of High Molecular Weight", *Analytical Chemistry*, Vol.25, no.10, p.1466 (1953). Viscosity index has been found to increase with lower branch ratio.

Oligomeric liquid lubricants exhibiting very low branch ratios have not previously been synthesized from 1-alkenes. Oligomers prepared from 1-decene, for example, by either cationic polymerization or Ziegler catalyst polymerization have branch ratios of greater than 0.20. Shubkin. *Ind. Eng. Chem. Prod. Res. Dev.* 1980, 19, 15–19, provides an explanation for the apparently limiting value for branch ratio based on a cationic polymerization reaction mechanism involving rearrangement to produce branching. Other explanations suggest isomerization of the olefinic group in the one position to produce an internal olefin as the cause for branching. Whether by rearrangement, isomerization or a mechanism which is yet to be elucidated, it is clear that the production of synthetic lubricants by the oligomerization of alkenes using conventional oligomerization catalysts results in excessive branching with the result that the limits of achievable lubricant properties, particularly the combination of high viscosity index and low pour point are severely constrained. Obviously, increased branching increases the number of isomers in the oligomer mixture, orienting the composition away from the structure which would be preferred for high viscosity although, as acountervailing factor, increased branching leads also to low product pour point, at least from a consideration of the theoretical concepts discussed above.

Recently, novel lubricant compositions comprising polyalpha-olefins and methods for their preparation have been disclosed in U.S. Pat. Nos. 4,827,064 and 4,827,073. The lubricant compositions, referred to in this specification as HVI-PAO, are made by the oligomerization of olefins such as 1-decene over a reduced Group VIB (IUPAC Table) metal catalyst, preferably chromium, and are characterized by a remarkable combination of properties: they possess very high viscosity index (VI) and low pour point. The VI may be as high as 150 or more and is typically 200 or even higher. The pour point (ASTM D-97 or equivalent) remains, however, low being typically below $-15°$ C. in the absence of any pour point improver. Reference is made to U.S. Pat. Nos. 4,827,064 and 4,827,073 for a description for a detailed disclosure of these HVI-PAO materials and their preparation.

The process for preparing the HVI-PAO lubricants comprises, as noted above, contacting a $C_6$–$C_{20}$ 1-alkene feedstock with reduced valence state chromium oxide catalyst on porous silica support under oligomerizing conditions in an oligomerization zone to produce the high viscosity, high VI liquid hydrocarbon lubricant with branch ratios less than 0.19 and pour points below $-15°$ C. The oligomerization temperature is typically maintained at a value between 90° and 250° C. to produce the lubricant viscosity product oligomers. These HVI-PAO lubricants cover a wide range of viscosities and may be used as high viscosity index lubricant basestocks after hydrogenation to remove residual unsaturation. The lubricant viscosity range materials exhibit a remarkably high VI and low pour point even at high viscosity.

By operating the oligomerization process at lower temperatures, higher viscosity materials may be produced and these materials may be used as viscosity index (VI) improvers for lubricants, both of mineral oil and synthetic origin, as described in U.S. patent application Serial No. 07/345,606, filed 1 May 1989 (Mobil Case 5362), to which reference is made for a description of these oligomers and of the way in which they are produced. The higher viscosity HVI-PAO products described in Serial No. 07/345,606 typically have viscosities between 725 and 15,000 cS at 100 C., corresponding to weight molecular weights from about 15,000 to 200,000 and number molecular weights from about 5,000 to about 50,000; carbon numbers for these molecular weights are from about $C_{30}$ to about $C_{10,000}$, with a preferred range from about $C_{30}$ to about $C_{5,000}$. These hydrocarbon oligomers are characterized by properties similar to those described in U.S. Pat. Nos. 4,827,064 and 4,827,073, namely, high VI coupled with excellent low temperature fluidity properties including pour point for the liquid products.

In the production of the HVI-PAO oligomers, oligomerization in a fixed bed reactor provides certain economic and process control advantages not readily achievable through other reactor and process configurations. However, the feasibility of fixed bed catalytic processing of 1-alkenes to prepare HVI-PAO lubricants depends upon an effective process for catalyst regeneration that will permit multiple regeneration cycles without significant loss in product yield or diminution of the unusual properties of HVI-PAO lubricants. Previous processes for the polymerization of 1-alkenes using catalysts similar to, although not identical to, the catalyst used in the HVI-PAO process were directed to high polymer preparation using very low concentration of catalyst. Hence, catalyst regeneration was not a requirement for process feasibility.

SUMMARY OF THE INVENTION

We have now developed an improved process for producing HVI-PAO type oligomers from alpha-olefins feedstock, such as 1-decene, which enables the catalyst to be readily regenerated. According to the present invention, the olefins are oligomerized to the desired products over a supported, reduced chromium catalyst to give the desired products. The catalyst is then regenerated to allow repeated recycling of the catalyst without a loss in yield of the HVI-PAO product.

The oligomers produced by the process have branch ratios below 0.19 and have a wide range of viscosities extending from the lubricant range to higher viscosity range materials which may be used, for example, as lubricant additives, especially VI improvers. The liquid oligomer products have higher viscosity indices than similar oligomers with higher branch ratios.

The regeneration process is useful for regenerating catalysts deactivated during the course of oligomerization at high temperatures to produce low viscosity HVI-PAO lubricants, as described in Ser. No. 07/282,362, but may also, and with advantage, be applied to the regeneration of catalysts produced in the oligomerization of products of higher viscosity, especially products of the type described in Ser. No. 07/345,606.

According to the present invention, the oligomerization catalyst is regenerated by stripping or purging the deactivated catalyst with inert gas at elevated temperature for a time sufficient to strip unreacted olefin and the oligomer product from the catalyst. The deactivated, stripped catalyst is then contacted with a stream of oxidizing gas while heating to elevated temperature to remove carbonaceous deposits, after which the oxidized catalyst is cooled and contacted with a stream of reducing gas to reduce the oxidized metal component of the oxidized catalyst to a lower valency state.

DESCRIPTION OF THE FIGURES

FIG. 1 is a plot of catalyst aging versus time-on-stream for the second cycle of the HVI-PAO process, FIG. 2 is a plot of the relationship between product yield and number of catalyst regenerations.

DETAILED DESCRIPTION

In the oligomerization process, the olefin feed is contacted with the oligomerization catalyst to produce the desired oligomer product. In the preparation of the liquid hydrocarbons suitable as lubricant basestocks an alpha-olefin feedstock comprising olefins of 6 to 20 carbon atoms, or mixtures of such olefins, is contacted with the oligomerization catalyst under oligomerization conditions, at a reaction temperature between 90 to 250 C dependent upon the desired product viscosity. The higher viscosity products are made at oligomerization temperatures from about $-20°$ to about $+90°$ C., with the exact temperature selected being dependent upon the viscosity desired in the product. Thus, in general, the oligomerization temperature may be from about $-20°$ to about 250° C., depending upon the characteristics, especially the viscosity, desired for the product.

In each case, the catalyst comprises a reduced metal oxide, preferably chromium, catalytic component on a porous support. The catalyst may be activated by treatment including oxidation at a temperature of 200° C. to 900° C. in the presence of an oxidizing gas and then by treatment with a reducing agent at a temperature and for a time sufficient to reduce the metal to a lower valence state.

Olefins suitable for use as starting material in the preparation of the HVI-PAO oligomers include those olefins containing from 2 to about 20 carbon atoms such as ethylene, propylene, 1-butene, 1-pentene, 1-hexene, 1-octene, 1-decene, 1-dodecene and 1-tetradecene and branched chain isomers such as 4-methyl-1-pentene. Also suitable for use are olefin-containing refinery feedstocks or effluents. However, the olefins used in this invention are preferably alpha olefinic as for example 1-heptene to 1-hexadecene and more preferably 1-octene to 1-tetradecene, or mixtures of such olefins.

The alpha-olefin oligomers are prepared by oligomerization reactions in which a major proportion of the double bonds of the alpha-olefins are not isomerized. These reactions include alpha-olefin oligomerization by supported metal oxide catalysts, such as Cr compounds on silica or other supported Group VIB compounds (IUPAC Periodic Table). The catalyst most preferred is a lower valence Group VIB metal oxide on a porous inert support. Preferred supports include silica, alumina, titania, silica alumina, magnesia and the like. The support material binds the metal oxide catalyst. Those porous substrates having a pore opening of at least 40 Å are preferred.

The support material usually has high surface area and large pore volumes with average pore size of 40 to about 350 Å. The high surface area are beneficial for supporting large amount of highly dispersive, active chromium metal centers and to give maximum efficiency of metal usage, resulting in very high activity catalyst. The support should have large average pore openings of at least 40 Å, with an average pore opening of 60 to 300 Å preferred. This large pore opening will not impose any diffusional restriction of the reactant and product to and away from the active catalytic metal centers, thus further optimizing the catalyst productivity. Also, for this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, $H_2$, $NH_3$, $H_2S$, $CS_2$, $CH_3SCH_3$, $CH_3SSCH_3$, metal alkyl containing compounds such as $R_3Al$, $R_3B$, $R_2Mg$, $RLi$, $R_2Zn$, where R is alkyl, alkoxy, aryl and the like. Preferred are CO or $H_2$ or metal alkyl containing compounds. Alternatively, the Group VIB metal may be applied to the substrate in reduced form, such as CrII compounds. The resultant catalyst is very active for oligomerizing olefins at a temperature range from below room temperature to about 250° C. at a pressure of 0.1 atmosphere to 5000 psi. Contact time of both the olefin and the catalyst can vary from one second to 24 hours. The catalyst can be used in a batch type reactor or in a fixed bed, continuous-flow reactor.

In general the support material may be added to a solution of the metal compounds, e.g., acetates or nitrates, etc., and the mixture is then mixed and dried at room temperature. The dry solid gel is purged with air at successively higher temperatures to about 600° for a period of about 16 to 20 hours. Thereafter the catalyst is cooled down under an inert atmosphere to a temperature of about 250 to 450° C. and a stream of reducing agent such as CO or $H_2$ is contacted therewith for a period to reduce the catalyst as indicated by a distinct color change from bright orange to bluish green. Typically, the catalyst is treated with an amount of CO equivalent to a two-fold stoichiometric excess to reduce the catalyst to a lower valence CrII state. Finally the catalyst is cooled down to room temperature and is ready for use.

The product oligomers have atactic molecular structure of mostly uniform head-to-tail connections with some head-to-head type connections in the structure. These low branch ratio oligomers have high viscosity indices at least about 15 to 20 units and typically 30-40 units higher than equivalent viscosity prior art oligomers, which regularly have higher branch ratios and correspondingly lower viscosity indices in the lubricant products. These low branch ratios are also correlated with the lour points of the lubricant products.

The branch ratios are defined as the ratios of $CH_3$ groups to $CH_2$ groups in the oligomers are calculated from the weight fractions of methyl groups obtained by infrared methods, published in *Analytical Chemistry*, Vol. 25, No.

$$\text{Branch ratio} = \frac{\text{wt fraction of methyl group}}{1 - (\text{wt fraction of methyl group})}$$

The liquid lubricant compositions produced by the oligomerization process at relatively high oligomerization temperatures e.g. between 90° and 250° C., comprise $C_{30}$-$C_{1300}$ hydrocarbons, with branch ratios of less than 0.19, weight average molecular weights between 300 and 45,000, number average molecular weights between 300 and 18,000. The molecular weight distribution of these oligomers is between 1 and 5 and the pour point of the liquid lubricants is below $-15°$ C.

Usually, the lubricant range oligomers are produced by varying the oligomerization temperature to yield lubricant viscosity range oligomers having weight average molecular weight between 420 and 45,000 and number average molecular weight between 420 and 18,000. Measured in carbon numbers, molecular weights range from $C_{30}$ to $C_{1300}$ and viscosity up to 750cs at 100° C., with a preferred range of $C_{30}$ to $C_{1000}$ and a viscosity of up to 500cS at 100° C. Molecular weight distributions (MWD), defined as the ratio of weight average molecular to number average molecular weight, range from 1.00 to 5, with a preferred range of 1.01 to 3 and a more preferred MWD of about 1.05 to 2.5. Compared to conventional PAO derived from $BF_3$ or $AlCl_3$ catalyzed polymerization of 1-alkene, HVI-PAO has been found to have a higher proportion of higher molecular weight polymer molecules in the product.

The viscosities of the lubricant HVI-PAO oligomers measured at 100 C range from 3 cS to 5000 cS. The viscosity index for the liquid polyalpha-olefins is approximately described by the following equation:

$$VI = 156.8 + 4.94 \times (V_{100°C.})^{0.5},$$

where $V_{100°C.}$ is the kinematic viscosity in centistokes measured at 100° C.

The higher viscosity oligomers produced at oligomerization temperatures below about 90° C. comprise hydrocarbons which have a branch ratio below 0.19 and a viscosity at 100° C. which is typically from 100 to 20,000 cS. The hydrocarbons typically have weight average molecular weights from 15,000 to 200,000 and number average molecular weights from 5,000 to 50,000 with a molecular weight distribution from about 1 to about 5. The viscosity index of the liquid compositions of this type is at least 130 and usually higher, for example, above 180 or even 200 or higher. The high viscosity materials are characterized by high shear stability, being stable under high temperature, high shear rate conditions, notably at 150° C. and a shear rate of one million ($10^6$) reciprocal seconds. Reference is made to Ser. No. 07/345,606 for a more detailed description of these oligomers, their properties and uses as well of the methods by which they may be made.

The HVI-PAO oligomers are usually hydrogenated after the oligomerization in keeping with the practice of hydrogenating the product to improve stability by removal of residual unsaturation. As oligomerized, the HVI-PAO oligomers are mixtures of dialkyl vinylidenic and 1,2 dialkyl or trialkyl mono-olefins. The lower molecular weight unsaturated oligomers are preferably hydrogenated to produce the thermally and oxidatively stable lubricants. The higher molecular weight unsaturated HVI-PAO oligomers are usually sufficiently thermally stable to be utilized without hydrogenation and, optionally, may be so employed. Both unsaturated and hydrogenated HVI-PAO of lower or higher molecular exhibit viscosity indices of at least 130 and pour point below 15° C.

During the production of synthetic lubricants made by reaction of 1-alkenes such as 1-decene over the reduced chromium/silica catalyst, catalyst deactivation occurs especially at the higher reaction temperatures used to produce the lubricant range products. This results in increasingly lower yields with time-on-stream. The yield of product reaches a point where it is not practical to continue the run. Therefore catalyst must be regenerated and restored to its original activity.

FIG. 1 shows a plot of catalyst aging expressed as time on stream compared to product yield for the second cycle preparation of 100cS (100° C.) HVI-PAO. Over the two month period a slight decrease in activity is noted. For the extruded catalyst a value of 0.4 is found by best fit of the data for the period between 20 to 52 days on stream. A somewhat greater rate of catalyst deactivation is experienced with a powdered catalyst.

The deactivated chromium catalysts used in the oligomerization process are regenerated by stripping the deactivated catalyst with inert gas at elevated temperature; contacting the stripped, deactivated catalyst with oxidizing gas while raising the catalyst temperature and holding said temperature for a time sufficient to oxidize said catalyst to hexavalent chromium and remove carbonaceous deposits. The oxidized, hexavalent chromium catalyst is then cooled and contacted with a reducing gas, preferably carbon monoxide or hydrogen, of which the former is the preferred species, at a temperature and for a time sufficient to reduce the hexavalent chromium to divalent chromium. The conditions used for the oxidation and reduction steps are comparable to those used in the initial catalyst activation procedure. Typical treatment regimes are illustrated in the Examples which follow.

The following Examples illustrate the preparation of HVI-PAO oligomers.

EXAMPLE 1

Catalyst Preparation and Activation Procedure 1.9 grams of chromium (II) acetate $(Cr_2(OCOCH_3)_4 2H_2O)$(5.58 mmole) (commercially obtained) is dissolved in 50 cc of hot acetic acid. Then 50 grams of a silica gel of 8-12 mesh size, a surface area of 300 $m^2/g$, and a pore volume of 1 cc/g, also is added. Most of the solution is absorbed by the silica gel. The final mixture is mixed for half an hour on a rotovap at room temperature and dried in an open-dish at room temperature. First, the dry solid (20 g) is purged with $N_2$ at 250° C. in a tube furnace. The furnace temperature is then raised to 400° C. for 2 hours. The temperature is then set at 600° C. with dry air purging for 16 hours. At this time the catalyst is cooled down under $N_2$ to a temperature of 300° C. Then a stream of pure CO (99.99% from Matheson) is introduced for one hour. Finally, the catalyst is cooled down to room temperature under $N_2$.

EXAMPLE 2

The powdered catalyst prepared in Example 1 (3.2 g) is packed in a ⅜" stainless steel tubular reactor inside an $N_2$ blanketed dry box. The reactor under $N_2$ atmosphere is then heated to 150° C. by a single-zone Lindberg furnace. Pre-purified 1-hexene is pumped into the reactor at 140 psi and 20 cc/hr. The liquid effluent is collected and stripped of the unreacted starting material and the low boiling material at 0.05 mm Hg. The residual clear, colorless liquid has viscosities and VI's suitable as a lubricant base stock.

| Sample | Prerun | 1 | 2 | 3 |
|---|---|---|---|---|
| T.O.S., hr. | 2 | 3.5 | 5.5 | 21.5 |
| Lube Yield, wt % | 10 | 41 | 74 | 31 |
| Viscosity, cS, at | | | | |
| 40° C. | 208.5 | 123.3 | 104.4 | 166.2 |
| 100° C. | 26.1 | 17.1 | 14.5 | 20.4 |
| VI | 159 | 151 | 142 | 143 |

The experiments conducted under the above condition of essentially constant temperature and WHSV produce HVI-PAO with about the same viscosity.

EXAMPLE 3

In a manner similar to that of Example 2, a fresh catalyst sample is charged into the reactor and 1-hexene is pumped to the reactor at 1 atm and 10 cc per hour. As shown below, a lube of high viscosities and high VI's is obtained. These runs show that at different reaction conditions, a lube product of high viscosities can be obtained and that viscosity can be varied with change in reaction temperature.

| Sample | A | B |
|---|---|---|
| T.O.S., hrs. | 20 | 44 |
| Temp., °C. | 100 | 50 |
| Lube Yield, % | 8.2 | 8.0 |
| Viscosities, cS at | | |
| 40° C. | 13170 | 19011 |
| 100° C. | 620 | 1048 |
| VI | 217 | 263 |

EXAMPLE 4

A commercial chrome/silica catalyst which contains 1% Cr on a large-pore volume synthetic silica gel is used. The catalyst is first calcined with air at 800° C. for 16 hours and reduced with CO at 300° C. for 1.5 hours. Then 3.5 g of the catalyst is packed into a tubular reactor and heated to 100° C. under the $N_2$ atmosphere. 1-Hexene is pumped through at 28 cc per hour at 1 atmosphere. The products are collected and analyzed as follows:

| Sample | C | D | E | F |
|---|---|---|---|---|
| T.O.S., hr. | 3.5 | 4.5 | 6.5 | 22.5 |
| Lube Yield, wt % | 73 | 64 | 59 | 21 |
| Viscosity, cS, at | | | | |
| 40° C. | 2548 | 2429 | 3315 | 9031 |
| 100° C. | 102 | 151 | 197 | 437 |
| VI | 108 | 164 | 174 | 199 |

These runs show that different Cr/silica catalyst are also effective for oligomerizing olefins to lube products.

EXAMPLE 5

As in Example 4, purified 1-decene is pumped through the reactor at 250 to 320 psi. The product is collected periodically and stripped of light products boiling points below 650° F. High quality lubes with high VI are obtained (see following table). The table also shows that at about the same WHSV, the viscosity of the product decreases with increasing reaction temperature (135, 166, 197° C.)

| Reaction Temp. °C. | WHSV g/g/hr | Lube Product Properties | | |
|---|---|---|---|---|
| | | V at 40° C. (cS.) | V at 100° C. (cS) | VI |
| 120 | 2.5 | 1555.4 | 157.6 | 217 |
| 135 | 0.6 | 389.4 | 53.0 | 202 |
| 150 | 1.2 | 266.8 | 36.2 | 185 |
| 166 | 0.6 | 67.7 | 12.3 | 181 |
| 197 | 0.5 | 21.6 | 5.1 | 172 |

The following Examples illustrate the regeneration of the HVI-PAO catalyst.

EXAMPLE 6

A. Catalyst Preparation 33 grams of 1/16 inch (1.59 mm) silica extrudates is placed into a 200 ml beaker. A solution of 1.52 grams of chromium acetate in 80 ml of water is added to the extrudates and allowed to stand overnight at room temperature. The excess water is removed by heating until the extrudates are damp. The damp extrudates are then placed into a rotovap at 80° C., under vacuum, and taken to dryness. Additional drying is made by vacuum drying at 120° C.. The resulting catalyst has the following properties:

| | |
|---|---|
| Catalyst Diameter, mm | 1.59 |
| Catalyst Length, mm | 6.35 |
| Surface Area, sq. M/Gm | 200 |
| Pore Diameter, Å | 200 |
| Chromium Loading, wt. % | 1.09 |
| Bulk Density, Gm/cc | 0.42 |

B. Catalyst Activation 10 grams (23 ml) of the above catalyst is placed into a stainless steel, fixed bed reactor whose inside diameter is ⅝ inches (15.9 mm). The length of the catalyst bed is six inches. The interstitial spaces between the extrudates is packed with 70/80 mesh sand. The chromium on silica extrudate catalyst is activated by predrying with dry nitrogen at 250° C., overnight. The catalyst bed is then calcined in air, at 200cc/min, from 250 to 600° C., at 1° C./minute and held at 600° C. for 12 hours. At the end of 12 hours, the temperature is reduced to 350° C. At this temperature, carbon monoxide, at 200 cc/min, is contacted with the catalyst for 30 minutes to reduce the chromium.

C. Pretreatment of 1-alkene

Prior to contacting the catalyst with the feed, the 1-alkene, such as 1-decene, is treated to remove catalyst poisons. The treatment consists of passing the feed over activated molecular sieves to remove traces of water and polar compounds such as decanol. The feed is further contacted with a reduced copper/chromia catalyst to remove peroxides. A final contact with predried 5A sieves is made. The feed pretreatment is made on a continuous basis before the feed enters the fixed bed reactor.

EXAMPLE 7

10 grams of the above activated extruded silica catalyst containing 1.09 wt. % chromium is placed into a fixed bed reactor. Synthetic HVI-PAO lubricants are then produced by feeding 1-decene to the catalyst bed at 125° C. reactor temperature and weight hourly space velocity (WHSV) based on catalyst of 2.2. Five reaction cycles are preformed with four regenerations between the cycles over a period of four months. The regeneration conditions and results are summarized in Table 1.

TABLE 1

| Regeneration Study - Chromium on Silica Extrudate | |
|---|---|
| Cycle | Product Yield, Wt % |
| 1 | 54.0 |
| 2 | 80.0 |
| 3 | 91.0 |
| 4 | 85.0 |
| 5 | 95.0 |

1. Oligomerization conditions - reactor temperature 125° C. and WHSV of 2.2.
2. Regeneration Conditions: Purge bed with nitrogen at 125° C. for one hour. Ramp temperature to 500° C. and hold for 12 hours. In air, heat from 100° C. to 600° C. at 1° C./min. and hold for 12 hours. Cool to 350° C. and contact catalyst bed with carbon monoxide at 350° C. and 200 cc/min. for 45 minutes.
3. Regeneration results: Run length - four months.

The purpose of the initial nitrogen purge and stripping at high temperatures is to remove as much 1-decene feed and product as possible prior to the air treatment step. The next step in the regeneration is to contact the chromium catalyst with a stream of air while raising the catalyst bed temperature from 100° C. to 600° C. at one degree per minute and holding the 600° C. temperature for 12 hours. The air contacting effectively removes any carbonaceous material from the catalyst and converts the chromium to a +6 (hexavalent) oxidation state. The last step in the regeneration is to cool the bed temperature to 350° C. while purging the bed with dry nitrogen. Once a bed temperature of 350° C. is achieved, carbon monoxide is introduced to the catalyst bed to reduce the chromium to the +2 (divalent) oxidation state and thereby reactivate the catalyst for further oligomerization of 1-decene to synthetic lubricant.

The time and temperature of the regeneration conditions in the above example are given only by way of example and are not intended to be limiting.

FIG. 2 shows a plot of product yield versus the number of regenerations for the above example and a similar study at 180° C. oligomerization temperature to produce 12cS (100° C.) HVI-PAO lubricant. It is clear from these data that the regeneration process can allow repeated oligomerization cycles in the HVI-PAO process without loss in yield or product properties. Indeed, the use of regenerated catalyst surprisingly and unexpectedly improves the yield of lubricant compared to fresh catalyst when the two catalysts are compared with other oligomerization conditions, primarily temperature, held constant. This unique discovery indicates that the reduced chromium catalyst on silica support is a superior catalyst to freshly prepared catalyst.

EXAMPLE 8

Two samples of 1.06% Cr on silica are calcined at 800° C. with air. Sample 1 is reduced with CO at 350° C. and sample 2 is reduced with $H_2$ at 300° C. The catalysts are tested for 1-hexene oligomerization at 60° C., as described before. The results are presented in Table 2.

TABLE 2

| Sample | 1 | 2 |
|---|---|---|
| lube yield, wt % | 84 | 12.5 |
| V @ 100° C., cS | 1882 | 737 |
| $(MW)_n \times 10^3$ | 4.53 | 2.9 |
| $(MW)_w \times 10^3$ | 18.75 | 12.4 |
| $Q = (MW)_x/(MW)_n$ | 4.14 | 4.2 |

These results show that, while CO reduction is preferred, $H_2$ reduction is effective in providing an oligomerization catalyst.

EXAMPLE 9

This Example illustrates the regeneration of the catalyst after preparation of a high viscosity oligomer product.

Catalyst Preparation:

50 gram silica gel, 8-12 mesh, (large pore silica from Alpha Chemical Co) was impregnated with 1.9g $Cr_2(OAc)_4.2H_2O$ in 50 cc acetic acid. The dried Cr/Silica gel was calcined with flowing air by gradually raising temperature to 600° C. for 16 hours. The catalyst was then cooled down to 350° C., purged with nitrogen to replace air and reduced with flowing CO gas for one hour. The catalyst was cooled down under nitrogen and stored in dry box under nitrogen atmosphere until use.

Polymerization and Catalyst Regeneration:

The catalyst, 3 g., was packed into a down-flow stainless steel tubular reactor and heated to desired reaction temperature. 1-Hexene was pumped through the reactor and product was collected at bottom of the reactor. The results were summarized below. At the end the catalyst seemed to have low activity. The catalyst was then purged with nitrogen to remove most organic components at 250° C. and calcined with air at 600° C., reduced with CO for half an hour. The calcination/reduction step was repeated once more, to make sure the catalyst was reactivated properly. The regenerated catalyst was very active for 1-hexene polymerization, as shown in the runs below.

| Run No. | 9-A | 9-B | 9-C | 9-D Catalyst Regenerated |
|---|---|---|---|---|
| Reaction temp. °C. | 100 | 60 | 150 | 150 |
| Pressure, psia | 15 | 15 | 15 | 270 |
| Feed Rate, g/g-cat/hr | 2.24 | 2.24 | 1.14 | 5.4 |
| Reaction time, hrs | 16 | 16 | 64 | 5.5 |
| Lube Yields, wt % | 8 | 8 | 2.5 | 82 |
| Lube Product Properties* | | | | |
| V @ 40° C. cS | 13169.7 | 19011.8 | — | 49.9 |
| V @ 100° C. cS | 619.9 | 1048.8 | — | 8.3 |
| VI | 217 | 264 | — | 140 |

*Lube product was isolated by distillation to remove light ends boiling below 120° C. at 0.1 mmHg.

We claim:

1. In a process for the preparation of olefin oligomers from alpha-olefin feedstock containing 6 to 20 carbon atoms, or mixtures of such olefins, comprising contacting said olefins under oligomerization conditions, at a reaction temperature between −20° to 250° C., and with a reduced chromium catalyst on a porous support, which catalyst has been treated by oxidation at a temperature of 200° to 900° C. in the presence of an oxidizing gas and then by treatment with a reducing agent at a temperature and for a time sufficient to reduce said catalyst to a lower valence state, to produce an olefin oligomer composition comprising $C_{30}$–$C_{10,000}$ hydrocarbons, said composition, having a branch ratio of less than 0.19, number average molecular weight between 420 and 45,000, weight average molecular weight between 420 and 200,000, and a molecular weight distribution between 1 and 5, while deactivating the catalyst the improvement comprising:

regenerating the deactivated chromium catalyst under regenerating conditions in a process comprising the steps of:
(a) stripping the deactivated catalyst with inert gas at an elevated temperature and for a time sufficient to strip unreacted olefin and oligomer product;
(b) contacting the deactivated, stripped catalyst with a stream of oxidizing gas while heating to an elevated temperature at a rate and for a time sufficient to oxidize the chromium of the catalyst and remove carbonaceous deposits from the catalyst;
(c) cooling the oxidized catalyst and contacting it with a stream of reducing gas in an amount sufficient and at a temperature and for a time sufficient to reduce the chromium of the oxidized catalyst to essentially lower valent chromium.

2. The process of claim 1 wherein step (b) oxidized catalyst comprises essentially hexavalent chromium.

3. The process of claim 1 wherein step (a) inert gas comprises nitrogen.

4. The process of claim 1 wherein said deactivated catalyst is stripped at a temperature of between 20 and 200° C. for about one hour and a temperature between 200 and 600° C. for about 12 hours.

5. The process of claim 1 wherein said oxidizing gas comprises air.

6. The process of claim 1 wherein step (b) stripped catalyst is heated from about 100° C. to 600° C. at a rate of about one degree Celsius per minute and maintained at about 600° C. for about 12 hours.

7. The process of claim 1 wherein step (c) oxidized catalyst is cooled to about 350° C. and said reducing gas comprises carbon monoxide at a temperature of about 350° C.

8. The process of claim 1 wherein the support comprises silica.

9. The process of claim 1 in which the olefin feedstock is oligomerized at a temperature from −20° to +90° C. to form an olefin oligomer having a branch ratio less than 0.19, a weight average molecular weight from about 15,000 to 200,000, a number average molecular weight from about 5,000 to about 50,000 and a molecular weight distribution from about 1 to about 5.

10. The process of claim 9 in which the olefin oligomer is shear stable under high temperature, high shear rate conditions of 150° C. and a shear rate of $10_6$ second$^{-1}$.

11. A process for oligomerizing alpha olefins to produce an oligomer hydrocarbon product including the steps of:
(a) contacting a $C_6$–$C_{20}$ alpha olefin with a supported solid reduced chromium oxide catalyst under oligomerization conditions at a temperature of about −20° to +250° C., said metal oxide comprising a lower valence form of at least one Group VIB metal to produce an olefin oligomer hydrocarbon product comprising $C_{30}$–$C_{10,000}$ hydrocarbons with a branch ratio of less than 0.19, a number average molecular weight between 420 and 45,000, a weight average molecular weight between 420 and 200,000, and a molecular weight distribution between 1 and 5, while deactivating the catalyst, (b) regenerating the deactivated reduced metal oxide catalyst under regenerating conditions in a process comprising the steps of:
  (i) stripping the deactivated catalyst with inert gas at elevated temperature and time sufficient to strip unreacted olefin and oligomer product;
  (ii) contacting the stripped, deactivated catalyst with a stream of oxidizing gas while heating to elevated temperature at a rate and for a time sufficient to oxidize the metal of the catalyst and remove carbonaceous deposits;
  (iii) cooling the oxidized catalyst and contacting it with a stream of reducing gas in an amount sufficient and at a temperature and for a time sufficient to reduce the oxidized metal of the catalyst to a lower valence state.

12. The process of claim 11 in which the metal oxide is chromium oxide; said support is silica, said reducing gas is carbon monoxide or hydrogen; and said lower valence state catalyst is essentially lower valent chromium.

13. The process of claim 11 in which the olefin feedstock is oligomerized at a temperature from $-20°$ to $+90°$ C. to form an olefin oligomer having a branch ratio less than 0.19, a weight average molecular weight from about 15,000 to 200,000, a number average molecular weight from about 5,000 to about 50,000 and a molecular weight distribution from about 1 to about 5.

14. The process of claim 11 in which the olefin oligomer is shear stable under high temperature, high shear rate conditions of $150°$ C. and a shear rate of $10^6$ second$^{-1}$.

15. The process of claim 11 in which the olefin is 1-decene.

* * * * *